United States Patent
Chen et al.

(10) Patent No.: US 11,834,425 B2
(45) Date of Patent: Dec. 5, 2023

(54) FULL CONTINUOUS-FLOW PREPARATION METHOD OF VITAMIN B1

(71) Applicant: Fudan University, Shanghai (CN)

(72) Inventors: Fener Chen, Shanghai (CN); Meifen Jiang, Shanghai (CN); Minjie Liu, Shanghai (CN); Yingqi Xia, Shanghai (CN); Weijian Li, Shanghai (CN)

(73) Assignee: Fudan University, Shanghai (CN)

( * ) Notice: Subject to any disclaimer, the term of this patent is extended or adjusted under 35 U.S.C. 154(b) by 0 days.

(21) Appl. No.: 18/166,478

(22) Filed: Feb. 9, 2023

(65) Prior Publication Data
US 2023/0183196 A1    Jun. 15, 2023

(30) Foreign Application Priority Data
Sep. 9, 2022    (CN) .......................... 202211106180.2

(51) Int. Cl.
*C07D 279/06*    (2006.01)
(52) U.S. Cl.
CPC .................. *C07D 279/06* (2013.01)
(58) Field of Classification Search
CPC .................................................. C07D 279/06
See application file for complete search history.

(56) References Cited

FOREIGN PATENT DOCUMENTS

AU          2018101877    *  1/2019

OTHER PUBLICATIONS

Williams et al, "Synthesis of vitamin B1", Journal of the American Chemical Society (1936), vol. 58 (8), pp. 1504-1505.
Matsukawa et al., "Studies on vitamin B1 and related compounds. XXII. Preparation of vitamin B1 from 3-[2'-methyl-4'-aminopyrimidyl-(5')]-methyl-4-methyl-5-beta-hydroxyethylthiiothiazolone (2)", Yakugaku Zasshi 1951; 71 (11): 1215-1218.
Gerard Moine et al., "A New Convergent Synthesis of Thiamine Hydrochloride", Helvetica Chimica Acta, vol. 73, (1990), pp. 1300-1305.
Todd et al., "73. Aneurin. Part VII. A synthesis of aneurin", Journal of the Chemical Society (Resumed), 1937, 364-367.

* cited by examiner

*Primary Examiner* — Samantha L Shterengarts
*Assistant Examiner* — Karen Cheng

(57) ABSTRACT

A full continuous-flow preparation method of vitamin $B_1$ includes: (S1) feeding 3-chloro-4-oxopentyl acetate, 2-methyl-4-amino-5-(aminomethyl) pyrimidine and carbon disulfide to a first continuous-flow reactor for addition; (S2) allowing the reaction mixture to flow into a first continuous filtration and reaction device to collect a filter cake; subjecting the filter cake and hydrochloric acid solution to cyclization; transporting the reaction mixture and an aqueous inorganic base solution to a micromixer and a second continuous-flow reactor for hydrolysis to obtain thiothiamine; (S3) transporting the thiothiamine to a third continuous-flow reactor with hydrogen peroxide for oxidation to obtain thiamine sulfate; and (S4) allowing the thiamine sulfate to enter a second continuous filtration and reaction device for filtration to collect a filter cake; and subjecting the filter cake to reaction with organic hydrochloric acid solution followed by filtration and drying to obtain vitamin $B_1$.

15 Claims, 2 Drawing Sheets

FULL CONTINUOUS-FLOW PREPARATION METHOD OF VITAMIN B1

CROSS-REFERENCE TO RELATED APPLICATIONS

This application claims the benefit of priority from Chinese Patent Application No. 202211106180.2, filed on Sep. 9, 2022. The content of the aforementioned application, including any intervening amendments thereto, is incorporated herein by reference in its entirety.

TECHNICAL FIELD

This application relates to organic synthesis, and more particularly to a full continuous-flow preparation method of vitamin $B_1$ (thiamine hydrochloride).

BACKGROUND

Vitamin $B_1$ has been widely employed as an anti-neuritic vitamin in the promotion of growth and health of animals and attracted considerable attention from both academia and pharmaceutical industry since it was isolated by Windaus from yeast in 1932. A great deal of effort has been invested to explore the synthesis strategies of vitamin $B_1$ (1):

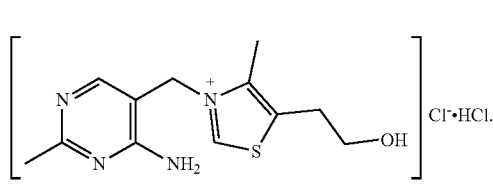

Synthesis routes published by Williams and Cline (Williams R. R. and Cline J. K., Synthesis of vitamin B1. J Am Chem Soc 1936; 58 (8):1504-1505.) and Matsukawa and Iwatsu (Matsukawa T. and Iwatsu T., "Studies on vitamin B1 and related compounds. 22. Preparation of vitamin B1 from 3-[T-methyl-4'-aminopyrimidyl-(5')]-methyl-4-methyl-5-beta-hydroxyethylthiothiazolone, "YAKUGAKU ZAS SHI 1951; 71 (11): 1215-1218.) are considered optimal for the industrial production of Vitamin $B_1$. Regarding the synthesis route proposed by Williams and Cline, 4-amino-5-bromomethyl-2-methylpyrimidine and thiazole are subjected to condensation to produce thiamine hydrobromide, which is further converted into thiamine hydrochloride (vitamin $B_1$) by ion exchange. As for the synthesis strategy developed by Todd and Bergel, a thiocarbonyl derivative of 2-methyl-4-amino-5-(aminomethyl) pyrimidine is synthesized, which further undergoes condensation with an open-chain chloro-ketone to obtain vitamin $B_1$. Modifications were made by Moine (*Chim. Acta*, 1990, 73, 1300) to such two preparation methods, in which Grewe diamine and mercaptoketone were subjected to condensation and cyclization to obtain vitamin $B_1$. This scheme has a simple preparation process, but it has high requirements for equipment and high production costs, and thus not suitable for the industrial production. At present, the most widely recognized in the industrial production is the route reported by Matsukawa (*Yakugaku Zasshi*, 1951, 71, 1215), which features simple operation and excellent atom economy. Unfortunately, due to the use of a traditional batch reactor, this method generally struggles with large time consumption, complicated treatment of intermediate products, cumbersome operation, and harsh temperature conditions, thereby limiting its industrial application.

SUMMARY

In view of the deficiencies of large time consumption, poor safety, high energy consumption and low efficiency in the existing vitamin $B_1$ synthesis approaches using a batch reactor, this application provides a full continuous-flow preparation method of vitamin $B_1$, which has shortened reaction time, improved yield and production efficiency, higher automation degree and safety, and less energy consumption, and thus exhibits brilliant industrial application prospects.

This application provides a full continuous-flow preparation method of vitamin $B_1$ using a continuous-flow reaction system, the continuous-flow reaction system including a first continuous-flow reactor, a first continuous filtration and reaction device, a micromixer, a second continuous-flow reactor, a third continuous-flow reactor, and a second continuous filtration and reaction device connected sequentially, and the full continuous-flow preparation method including:

(S1) feeding 3-chloro-4-oxopentyl acetate (3), 2-methyl-4-amino-5-(aminomethyl) pyrimidine (2) and carbon disulfide to the first continuous-flow reactor for addition reaction to obtain a first reaction mixture;

(S2) allowing the first reaction mixture to flow from the first continuous-flow reactor into the first continuous filtration and reaction device for filtration to collect a first filter cake; subjecting the first filter cake and a hydrochloric acid solution to cyclization reaction to obtain a second reaction mixture; and transporting the second reaction mixture together with an aqueous inorganic base solution to the micromixer and the second continuous-flow reactor for hydrolysis reaction to obtain thiothiamine (5);

(S3) transporting the thiothiamine and hydrogen peroxide to the third continuous-flow reactor for oxidation reaction to obtain thiamine sulfate (6); and (S4) allowing the thiamine sulfate to enter the second continuous filtration and reaction device for filtration to collect a second filter cake; and subjecting the second filter cake to reaction with an organic hydrochloric acid solution followed by filtration and drying to obtain thiamine hydrochloride (1) as the vitamin $B_1$; as shown in the following reaction scheme:

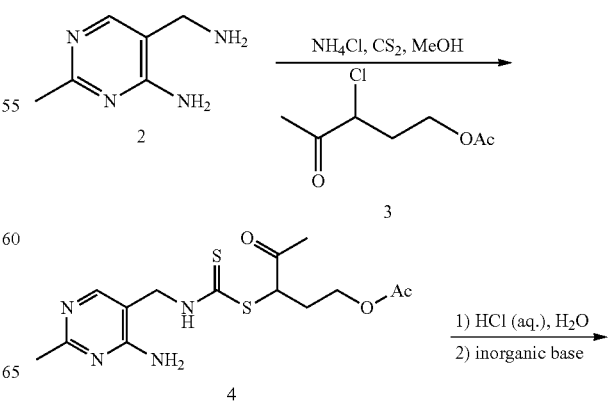

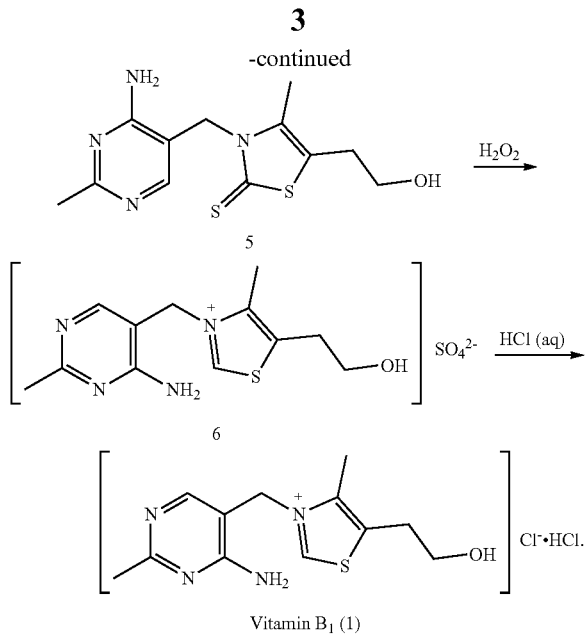

Vitamin B₁ (1)

In an embodiment, in step (S1), the 3-chloro-4-oxopentyl acetate (3) is pure 3-chloro-4-oxopentyl acetate or a solution of the 3-chloro-4-oxopentyl acetate (3) in an organic solvent; and the organic solvent is selected from the group consisting of an alcohol solvent, an ether solvent, an ester solvent and a ketone solvent. In an embodiment, the 3-chloro-4-oxopentyl acetate (3) is a solution of the 3-chloro-4-oxopentyl acetate (3) in an organic solvent.

In an embodiment, in step (S1), flow rates of the 3-chloro-4-oxopentyl acetate (3), 2-methyl-4-amino-5-(aminomethyl) pyrimidine (2) and carbon disulfide are controlled such that a molar ratio of the 3-chloro-4-oxopentyl acetate (3) to the carbon disulfide to the 2-methyl-4-amino-5-(aminomethyl) pyrimidine (2) is (0.9~5):(0.9~5): 1, preferably (1~3):(1~3): 1. Specifically, 2-methyl-4-amino-5-(aminomethyl) pyrimidine (2) is prepared according to the method in Chinese patent No. 112341395B.

In an embodiment, in step (S1), the addition reaction is performed in the first continuous-flow reactor at 0~80° C. and 0~1 MPa for 0.5~60 min, preferably at 20~60° C. and 0~0.3 MPa for 10~40 min.

In an embodiment, in step (S2), in the first continuous filtration and reaction device, the filtration is performed at −10~30° C., preferably −5~10° C.; and the cyclization reaction is performed at 20~100° C., preferably 50~70° C.

In an embodiment, in step (S2), flow rates of the first reaction mixture and the hydrochloric acid solution are controlled such that a molar ratio of an intermediate (4) in the first filter cake to hydrochloric acid is 1:(0.5~6), preferably 1:(1~3).

In an embodiment, in step (S2), flow rates of the second reaction mixture and the aqueous inorganic base solution are controlled such that a molar ratio of a cyclization product in the second reaction mixture to an inorganic base is 1:(1~10), preferably 1:(1~4).

In an embodiment, a temperature of the micromixer is controlled to 0~40° C., preferably 20~40° C.; and the hydrolysis reaction is performed in the second continuous-flow reactor at 20~120° C. for 0.1~60 min, preferably at 30~80° C. for 0.230 min. In an embodiment, in step (S2), a temperature of the second continuous-flow reactor is controlled to −10~80° C., preferably 20~60° C.; and a pressure of the second continuous-flow reactor is controlled to 0~1 MPa, preferably 0~0.3 MPa.

In an embodiment, in step (S2), a mass percentage of an inorganic base in the aqueous inorganic base solution is 5~50%, preferably 10~30%. In an embodiment, the inorganic base is selected from the group consisting of lithium carbonate, sodium carbonate, potassium carbonate, lithium bicarbonate, sodium bicarbonate, potassium bicarbonate, ammonia, ammonium carbonate, ammonium chloride, ammonium bicarbonate, lithium bicarbonate, sodium bicarbonate, potassium bicarbonate, lithium hydroxide, sodium hydroxide, potassium hydroxide and a combination thereof, preferably sodium bicarbonate, sodium carbonate, sodium hydroxide or potassium hydroxide.

In an embodiment, the first continuous filtration and reaction device and the second continuous filtration and reaction device are independently a continuous kettle filter, a continuous scraper filter, a continuous filter press and a continuous rotary disc filter or a combination thereof connected in series with a reactor.

In an embodiment, in step (S3), a molar ratio of the thiothiamine (5) to the hydrogen peroxide is 1:(0.9~5), preferably 1:(1.2~4).

In an embodiment, in step (S3), the oxidation reaction is performed in the third continuous-flow reactor at −10~50° C. and 0~1 MPa for 0.1~60 min, preferably at 10~50° C. and 0~0.3 MPa for 0.1~40 min.

In an embodiment, in step (S4), the filtration in the second continuous filtration and reaction device is performed at −15~30° C., preferably 0~10° C.; and the reaction between the second filter cake and the organic hydrochloric acid solution is performed at 20~100° C. and 0~1 MPa for 0.1~60 min, preferably at 30~60° C. and 0~0.3 MPa for 1~40 min.

In an embodiment, in step (S4), a molar ratio of the thiamine sulfate (6) in the second filter cake to hydrochloric acid 1:(0.9~5), preferably 1:(1~3).

In an embodiment, in step (S4), the organic hydrochloric acid solution is selected from the group consisting of hydrochloride methanol solution, hydrochloride ethanol solution, hydrochloride ethylene glycol solution, hydrochloride propanol solution, hydrochloride acetone solution, hydrochloride ethyl acetate solution and hydrochloride dioxane solution.

In an embodiment, the first continuous-flow reactor, the second continuous-flow reactor and the third continuous-flow reactor are independently a microchannel continuous-flow reactor, a static tubular continuous-flow reactor, an oscillatory tubular continuous-flow reactor or an oscillatory plate-type continuous-flow reactor; an inner diameter of the static tubular continuous-flow reactor and the oscillatory tubular continuous-flow reactor is 1 mm-20 cm, such as 2 mm-10 cm; and an inner diameter of the oscillatory plate-type continuous-flow reactor is 500 μm~5 cm, such as 100 μm~2.5 cm.

In an embodiment, in step (S2), the micromixer is a static mixer, a T-type mixer, a Y-type mixer, a cross-type mixer, a coaxial flow mixer, a continuous stirring mixer or a flow-focusing mixer; the first continuous-flow reactor, the second continuous-flow reactor and the third continuous-flow reactor are each formed by one or more continuous-flow reactors connected in series or in parallel; and the first continuous filtration and reaction device and the second continuous filtration and reaction device are each formed by one or more continuous filtration and reaction devices connected in series or in parallel.

In an embodiment, the continuous-flow reaction system further includes a first feed pump, a second feed pump, a third feed pump, a fourth feed pump, a fifth feed pump, a sixth feed pump, a seventh feed pump, a first control valve, a second control valve, a third control valve, a fourth control valve and a fifth control valve; an inlet of the first continuous-flow reactor is connected to the first feed pump, the second feed pump and the third feed pump; an outlet of the first continuous-flow reactor is connected to a first inlet of the first continuous filtration and reaction device; a second inlet of the first continuous filtration and reaction device is connected to the fourth feed pump through the first control valve; an outlet of the first continuous filtration and reaction device is connected to a first port of the second control valve; a second port of the second control valve is connected to a first filtrate collection pipeline; a third port of the second control valve is connected to the fifth feed pump; the fifth feed pump is connected to a first inlet of the micromixer; a second inlet of the micromixer is connected to the sixth feed pump; an outlet of the micromixer is connected to the second continuous-flow reactor; an outlet of the second continuous-flow reactor is connected to a first inlet of the second continuous filtration and reaction device through the third control valve; a second inlet of the second continuous filtration and reaction device is connected to the seventh feed pump through the fourth control valve; an outlet of the second continuous filtration and reaction device is connected to a first port of the fifth control valve; a second port of the fifth control valve is connected to a second filtrate collection pipeline which is connected to a recovery system, and a third port of the fifth control valve is connected to a target product collection pipeline.

In an embodiment, the continuous-flow reaction system further includes a first feed pump, a second feed pump, a third feed pump, a fourth feed pump, a fifth feed pump, a sixth feed pump, a seventh feed pump, a first control valve, a second control valve, a third control valve, a fourth control valve, a fifth control valve, and a buffer tank; an inlet of the first continuous-flow reactor is connected to the first feed pump, the second feed pump and the third feed pump; an outlet of the first continuous-flow reactor is connected to a first inlet of the first continuous filtration and reaction device; a second inlet of the first continuous filtration and reaction device is connected to the fourth feed pump through the first control valve; an outlet of the first continuous filtration and reaction device is connected to a first port of the second control valve; a second port of the second control valve is connected to a first filtrate collection pipeline; a third port of the second control valve is connected to an inlet of the buffer tank; the outlet of the buffer tank is connected to a fifth feed pump; the fifth feed pump is connected to a first inlet of the micromixer; a second inlet of the micromixer is connected to the sixth feed pump; an outlet of the micromixer is connected to the second continuous-flow reactor; an outlet of the second continuous-flow reactor is connected to a first inlet of the second continuous filtration and reaction device through the third control valve; a second inlet of the second continuous filtration and reaction device is connected to the seventh feed pump through the fourth control valve; an outlet of the second continuous filtration and reaction device is connected to a first port of the fifth control valve; a second port of the fifth control valve is connected to a second filtrate collection pipeline, and a third port of the fifth control valve is connected to a target product collection pipeline.

Compared to the prior art, this application has the following beneficial effects.

1. Compared with the existing synthesis methods using a traditional batch reactor, the continuous-flow reaction system has the advantages of high mass and heat transfer efficiencies and superior mixing performance, which greatly shortens the reaction time (from several days to several hours or even tens of minutes), and greatly improves the reaction efficiency, and minimizes the side reaction while reaching a yield similar to that of the traditional batch synthesis method.

2. The continuous and automatic synthesis from raw materials to the target product is enabled, allowing for high spatio-temporal efficiency, lowered labor intensity and low production cost.

3. The 2-methyl-4-amino-5-(aminomethyl) pyrimidine, 3-chloro-4-oxopentyl acetate and carbon disulfide can be fed and react in a relatively closed continuous channel, and at the same time, the amount of individual raw materials can be accurately controlled. The continuous oxidation reaction of thiothiamine and hydrogen peroxide is performed in the channel of the continuous-flow reactor, which brings small reaction volume, low online liquid holdup and improved safety.

4. The multiphase mixing, reaction and mass transfer processed are all completed in the micromixer, continuous filtration and reaction device and continuous-flow reactor, which leads to simple and efficient operation, less energy and time consumption, and low cost.

5. The full continuous-flow preparation method can be easily industrialized through a multi-channel parallel scale-up strategy, facilitating the industrial production of vitamin $B_1$.

In the figures: 1-first feed pump; 2-second feed pump; 3-third feed pump; 4-first continuous-flow reactor; 5-fourth feed pump; 6-first control valve; 7-first continuous filtration and reaction device; 8-first filtrate collection pipeline; 9-second control valve; 10-fifth feed pump; 11-sixth feed pump; 12-micromixer; 13-second continuous-flow reactor; 14-seventh feed pump; 15-third continuous-flow reactor; 16-third control valve; 17-eighth feed pump; 18-fourth control valve; 19-second continuous filtration and reaction device; 20-second filtrate collection pipeline; 21-target product collection pipeline; 22-third continuous filtration and reaction device; 23-fourth continuous filtration and reaction device; 24-fifth control valve; 25-sixth control valve; and 26-buffer tank.

DETAILED DESCRIPTION OF EMBODIMENTS

The structure features, technical solutions, objects and beneficial effects of the disclosure will be described in detail below with reference to the embodiments and drawings. The embodiments are merely illustrative of the disclosure, and are not intended to limit the disclosure.

Figure 1:
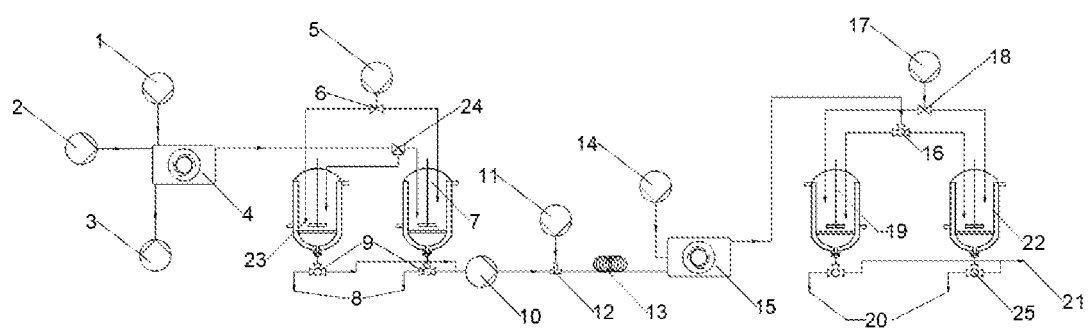
FIG. 1 structurally illustrates a continuous-flow preparation system of vitamin $B_1$ according to an embodiment of the present disclosure.
Figure 2:
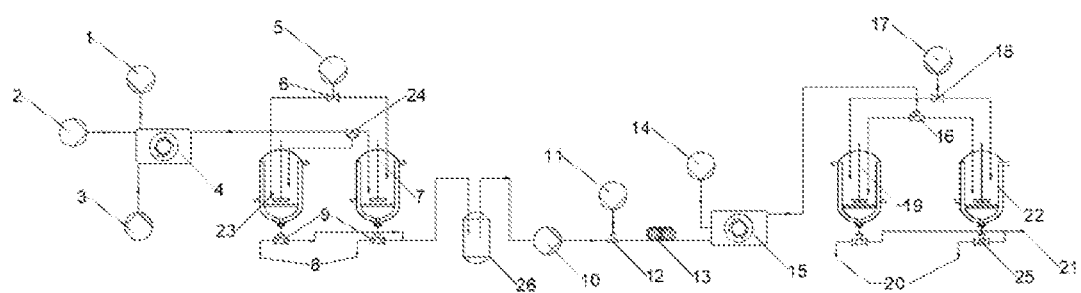
FIG. 2 structurally illustrates a continuous-flow preparation system of vitamin $B_1$ according to another embodiment of the present disclosure.

As shown in FIG. 1, a continuous-flow reaction system used in the preparation method includes a first feed pump 1 for feeding 3-chloro-4-oxopentyl acetate, a second feed pump 2 for feeding carbon disulfide, a third feed pump 3 for feeding 2-methyl-4-amino-5-(aminomethyl) pyrimidine, a first continuous-flow reactor 4, a fourth feed pump 5 for feeding a hydrochloric acid solution, a first control valve 6, a first continuous filtration and reaction device 7, a first filtrate collection pipeline 8, a second control valve 9, a fifth feed pump 10, a sixth feed pump 11 for feeding an aqueous inorganic base solution, a micromixer 12, a second continuous-flow reactor 13, a seventh feed pump 14 for feeding hydrogen peroxide, a third continuous-flow reactor 15, a third control valve 16, an eighth feed pump 17 for feeding an organic hydrochloric acid solution, a fourth control valve 18, a second continuous filtration and reaction device 19, a second filtrate collection pipeline 20, a target product collection pipeline 21, a third continuous filtration and reaction device 22, a fourth continuous filtration and reaction device 23, a fifth control valve 24, a sixth control valve 25, and a buffer tank 26.

An inlet of the first continuous-flow reactor 4 is connected to the first feed pump 1, the second feed pump 2 and the third feed pump 3. An outlet of the first continuous-flow reactor 4 is connected to the fifth control valve 24, and an outlet of the fifth control valve 24 is connected to a first inlet of the first continuous filtration and reaction device 7 and a first inlet of the fourth continuous filtration and reaction device 23 connected in parallel with the first continuous filtration and reaction device 7. A second inlet of the first continuous filtration and reaction device 7 and a second inlet of the fourth continuous filtration and reaction device 23 are connected to the fourth feed pump 5 through the first control valve 6. An outlet of the first continuous filtration and reaction device 7 is connected to a first port of the second control valve 9. A second port of the second control valve 9 is connected to the first filtrate collection pipeline 8. A third port of the second control valve 9 is connected to the fifth feed pump 10. The fifth feed pump 10 is connected to a first inlet of the micromixer 12. A second inlet of the micromixer 12 is connected to the sixth feed pump 11. An outlet of the micromixer 12 is connected to the second continuous-flow reactor 13. An outlet of the second continuous-flow reactor 13 is connected to a first inlet of the second continuous filtration and reaction device 19 through the third control valve 16. A second inlet of the second continuous filtration and reaction device 19 is connected to the eighth feed pump 17 through the fourth control valve 18. An outlet of the second continuous filtration and reaction device 19 is connected to a first port of the sixth control valve 25. A second port of the sixth control valve 25 is connected to the second filtrate collection pipeline 20 which is connected to a recovery system, and a third port of the sixth control valve 25 is connected to the target product collection pipeline 21.

An operation process of the above continuous-flow reaction system is described as follows.

(S1) 3-chloro-4-oxopentyl acetate, carbon disulfide and 2-methyl-4-amino-5-(aminomethyl) pyrimidine are fed respectively by the first feed pump 1, the second feed pump 2 and the third feed pump 3 to the first continuous-flow reactor 4 for addition reaction. Then the reaction mixture flows from the first continuous-flow reactor 4 into the first continuous filtration and reaction device 7 for filtration. The filtrate flows into the first filtrate collection pipeline 8 through the second port of the second control valve 9, and the filter cake and the hydrochloric acid solution fed by the fourth feed pump 5 undergoes cyclization reaction in the first continuous filtration and reaction device 7.

(S2) The reaction mixture passes through the third port of the second control valve 9 and is fed by the fifth feed pump 10 to the micromixer 12, to which the aqueous inorganic base solution is simultaneously fed by the sixth feed pump 11. Then the reaction mixture enters the second continuous-flow reactor 13 for hydrolysis reaction.

(S3) The reaction mixture flows from the second continuous-flow reactor 13 into the third continuous-flow reactor 15 for oxidation reaction with hydrogen peroxide fed by the seventh feed pump 14.

(S4) The reaction mixture flowing out of the third continuous-flow reactor 15 passes through the third control valve 16 and enters the second continuous filtration and reaction device 19 for continuous filtration, where the filtrate flows into the second filtrate collection pipeline 20 through the second port of the sixth control valve 25, and the filter cake reacts with the organic hydrochloric acid solution fed by the eighth feed pump 17 in the second continuous filtration and reaction device 19. The reaction mixture passes through the sixth control valve 25 to enter the target product collection pipeline 21, and is then subjected to filtration and drying to obtain thiamine hydrochloride solid (vitamin $B_1$).

To make the objects, technical solutions and beneficial effects of the disclosure clearer, the disclosure will be further described in detail in conjunction with the following embodiments.

Example 1

3-chloro-4-oxopentyl acetate liquid, carbon disulfide and 2-methyl-4-amino-5-(aminomethyl) pyrimidine were simultaneously fed to the first continuous-flow reactor (a tubular reactor with a reaction volume of 10 mL and a microchannel diameter of 2.5 cm) for addition reaction, where flow rates of the 3-chloro-4-oxopentyl acetate liquid, carbon disulfide and 2-methyl-4-amino-5-(aminomethyl) pyrimidine were adjusted such that a molar ratio of 3-chloro-4-oxopentyl acetate to carbon disulfide to 2-methyl-4-amino-5-(aminomethyl) pyrimidine was 1.2:1.3:1. The back pressure in the first continuous flow tubular reactor 4 was set to 0 MPa, and the temperature in the first continuous-flow reactor 4 was 50° C. After reacted for 10 min (namely, a residence time of the reaction mixture in the first continuous-flow reactor 4 was 10 min), the reaction mixture flowed out of the first continuous-flow reactor 4 and entered the first continuous filtration and reaction device 7 (continuous kettle filter) for continuous filtration to collect a filter cake, where the reaction mixture was sampled and analyzed, and the results indicated that the conversion rate of 2-methyl-4-amino-5-(aminomethyl) pyrimidine was 100%, and the purity of the intermediate (4) was greater than 99%. Then the hydrochloric acid solution was fed into the continuous filtration and reaction device 7 through the control valve to react with the filter cake at 78° C. for 15 min. At the same time, the reaction mixture flowed out of the first continuous-flow reactor 4 and entered the fourth continuous filtration and reaction device 23 (kettle filter) through the fifth control valve 24 for continuous filtration, where the filtration was performed at 20° C. The flow rates were adjusted such that a molar ratio of the intermediate (4) to hydrochloric acid was 1:1.5.

After that, the reaction mixture and the aqueous sodium hydroxide solution were simultaneously fed to the micromixer 12 (T-type mixer) and the second continuous-flow reactor 13 (microchannel reactor) in sequence. Flow rates of the reaction mixture and the aqueous sodium hydroxide solution were adjusted such that the pH value for the reaction mixture was 6.5-7.5. The temperature in the micromixer 12 was set to 25° C., and the reaction in the second continuous-flow reactor 13 was performed at 25° C. and 0.2 MPa for 2 min. The reaction mixture was sampled and analyzed, and the results revealed that the purity of the intermediate (5) was greater than 98%.

The reaction mixture then entered the third continuous-flow reactor 15 (oscillatory tubular continuous-flow reactor) and underwent oxidation reaction with hydrogen peroxide fed by the seventh feed pump 14, where a molar ratio of the intermediate (5) to hydrogen peroxide was controlled to 1:1.05. In the third continuous-flow reactor 15, the oxidation was performed at 25° C. and 0 MPa for 30 min, where the reaction mixture was sampled and analyzed, and the results indicated that the conversion rate was greater than 98%.

The reaction mixture entered the second continuous filtration and reaction device 19 (continuous kettle filter), and was filtered at 0° C., and the hydrochloride ethanol solution was fed to the second continuous filtration and reaction device 19 through the fourth control valve 18 to react with the filter cake. At the same time, the reaction mixture flowed out of the third continuous-flow reactor 15 and entered the third continuous filtration and reaction device 22 (continuous kettle filter) through the third control valve 16 for continuous filtration. The reaction was performed at 60° C. for 15 min, and a molar ratio of the intermediate (6) to hydrochloric acid was controlled to 1:1.15. The filtration was continued at a temperature of 0° C., and the filtrate was collected through the second filtrate collection pipeline 20. The filter cake was dried to obtain vitamin $B_1$ (70.2% yield, and 98.8% purity).

Example 2

This example was basically the same as Example 1 except that in this example, the continuous-flow reactor in the first step was an oscillatory plate-type continuous-flow reactor with a volume of 90 mL and an inner diameter of 2 mm; the addition reaction was performed at 60° C. for 45 min; and the oxidation reaction was performed at 40° C. for 20 min. In this example, the 2-methyl-4-amino-5-(aminomethyl) pyrimidine was almost completely converted, and the resultant vitamin $B_1$ had a purity of 99% and a total separation yield of 68.5%.

Example 3

This example was basically the same as Example 1 except that in this example, the reaction mixture after the cyclization reaction did not directly undergo the hydrolysis reaction but collected by the buffer tank 26. Then the reaction mixture was transported by the fifth feed pump 10 to the second continuous-flow reactor 13 for reaction with sodium hydroxide solution. In this example, the 2-methyl-4-amino-5-(aminomethyl) pyrimidine was almost completely converted, and the resultant vitamin $B_1$ had a purity of 98.9% and a total separation yield of 72%.

Example 4

This example was basically the same as Example 1 except that in this example, the molar ratio of the 3-chloro-4-oxopentyl acetate to the carbon disulfide to the 2-methyl-4-amino-5-(aminomethyl) pyrimidine was 1.1:1:1, and the temperature in the first continuous-flow reactor 4 was 40° C. In this example, a conversion rate of the 2-methyl-4-amino-5-(aminomethyl) pyrimidine was 92%, and the resultant vitamin $B_1$ had a purity of 98% and a total separation yield of 40.2%.

Example 5

This example was basically the same as Example 1 except that in this example, the cyclization reaction was performed at 85° C. for 30 min, and the molar ratio of the intermediate (4) to hydrochloric acid was 1:2. In this example, the conversion rate of the 2-methyl-4-amino-5-(aminomethyl) pyrimidine was 99%, and the resultant vitamin $B_1$ had a purity of 98.7% and a total separation yield of 72.4%.

Example 6

This example was basically the same as Example 1 except that in this example, the micromixer was a Y-type mixer; a mixing temperature was set to 30° C.; and the hydrolysis reaction was performed at 35° C. and 0 MPa for 0.5 min. In this example, the conversion rate of the 2-methyl-4-amino-5-(aminomethyl) pyrimidine was 100%, and the resultant vitamin $B_1$ had a purity of 99.4% and a total separation yield of 70.2%.

Example 7

This example was basically the same as Example 1 except that in this example, in the hydrolysis reaction, an aqueous potassium bicarbonate solution with a mass percentage of 15% was used. The resultant vitamin $B_1$ had a purity of 98% and a total separation yield of 70.3%.

Example 8

This example was basically the same as Example 1 except that in this example, the organic hydrochloric acid solution was hydrochloride ethylene glycol solution, the molar ratio of the thiamine sulfate (6) and the organic hydrochloric acid solution was adjusted to 1:3, the reaction temperature was 80° C., and the filtration temperature was −15° C. In this example, the conversion rate of the 2-methyl-4-amino-5-(aminomethyl) pyrimidine was 99%, and the resultant vitamin $B_1$ had a purity of 99% and a total separation yield of 68.0%.

Example 9

This example was basically the same as Example 1 except that in this example, the continuous filtration and reaction devices were each a combined device of a continuous rotary disc filter and a continuous kettle filter. In this example, the resultant vitamin $B_1$ had a purity of 95% and a total separation yield of 53%.

Example 10

This example was basically the same as Example 1 except that in this example, the molar ratio of the 3-chloro-4-oxopentyl acetate to the carbon disulfide to the 2-methyl-4-amino-5-(aminomethyl) pyrimidine was 2:1.5:1. The conversion rate of the 2-methyl-4-amino-5-(aminomethyl) pyrimidine was 100%, and the resultant vitamin $B_1$ had a purity of 98% and a total separation yield of 71.2%.

Example 11

This example was basically the same as Example 1 except that in this example, the 3-chloro-4-oxopentyl acetate used methyl alcohol as solvent. In this example, the conversion rate of the 2-methyl-4-amino-5-(aminomethyl) pyrimidine was 100%, and the resultant vitamin $B_1$ had a purity of 99% and a total separation yield of 69.7%.

Although the present disclosure has been described in detail above with reference to the embodiments, those skilled in the art can still make some modifications, replacements and variations thereto. Understandably, any modifications and replacements made by those skilled in the art without departing from the spirit of the disclosure should fall within the scope of the disclosure defined by the appended claims.

What is claimed is:

1. A full continuous-flow preparation method of vitamin $B_1$ using a continuous-flow reaction system, the continuous-flow reaction system comprising a first continuous-flow reactor, a first continuous filtration and reaction device, a micromixer, a second continuous-flow reactor, a third continuous-flow reactor, and a second continuous filtration and reaction device connected sequentially, and the full continuous-flow preparation method comprising:

(S1) feeding 3-chloro-4-oxopentyl acetate (3), 2-methyl-4-amino-5-(aminomethyl) pyrimidine (2) and carbon disulfide to the first continuous-flow reactor for addition reaction to obtain a first reaction mixture;

(S2) allowing the first reaction mixture to flow from the first continuous-flow reactor into the first continuous filtration and reaction device for filtration to collect a first filter cake; subjecting the first filter cake and a hydrochloric acid solution to cyclization reaction to obtain a second reaction mixture; and transporting the second reaction mixture together with an aqueous inorganic base solution to the micromixer and the second continuous-flow reactor for hydrolysis reaction to obtain thiothiamine (5);

(S3) transporting the thiothiamine and hydrogen peroxide to the third continuous-flow reactor for oxidation reaction to obtain thiamine sulfate (6); and (S4) allowing the thiamine sulfate to enter the second continuous filtration and reaction device for filtration to collect a second filter cake; and subjecting the second filter cake to reaction with an organic hydrochloric acid solution followed by filtration and drying to obtain thiamine hydrochloride (1) as the vitamin $B_1$; as shown in the following reaction scheme:

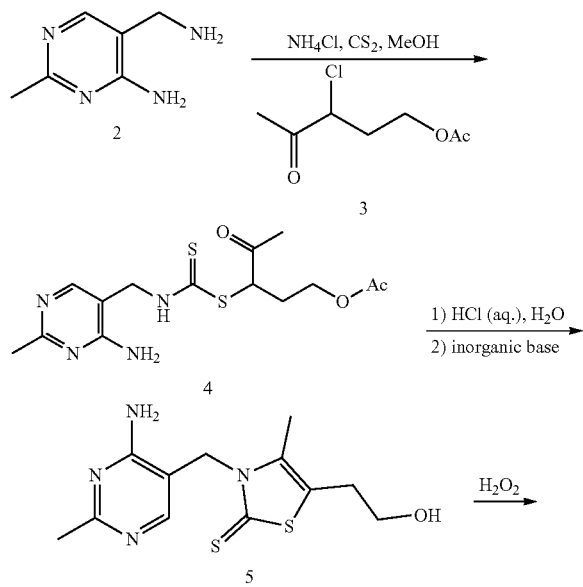

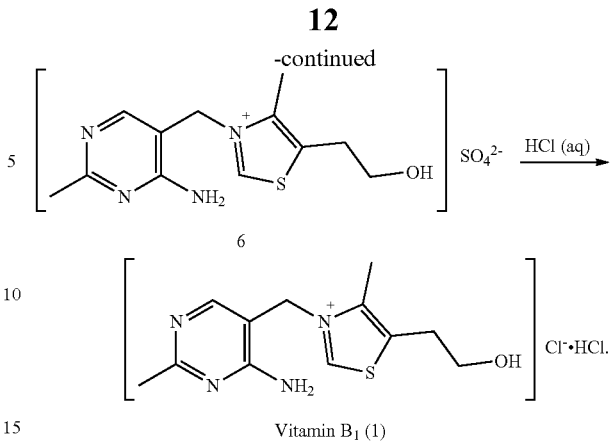

Vitamin $B_1$ (1)

2. The full continuous-flow preparation method of claim 1, wherein in step (S1), the 3-chloro-4-oxopentyl acetate (3) is pure 3-chloro-4-oxopentyl acetate or a solution of the 3-chloro-4-oxopentyl acetate (3) in an organic solvent; and the organic solvent is selected from the group consisting of an alcohol solvent, an ether solvent, an ester solvent and a ketone solvent.

3. The full continuous-flow preparation method of claim 1, wherein in step (S1), flow rates of the 3-chloro-4-oxopentyl acetate (3), 2-methyl-4-amino-5-(aminomethyl) pyrimidine (2) and carbon disulfide are controlled such that a molar ratio of the 3-chloro-4-oxopentyl acetate (3) to the carbon disulfide to the 2-methyl-4-amino-5-(aminomethyl) pyrimidine (2) is (0.9-5):(0.9-5): 1.

4. The full continuous-flow preparation method of claim 1, wherein in step (S1), the addition reaction is performed in the first continuous-flow reactor at 0-80° C. and a 0-1 MPa for 0.5-60 min.

5. The full continuous-flow preparation method of claim 1, wherein in step (S2), in the first continuous filtration and reaction device, the filtration is performed at −10-30° C., and the cyclization reaction is performed at 20-100° C.; and flow rates of the first reaction mixture and the hydrochloric acid solution are controlled such that a molar ratio of an intermediate (4) in the first filter cake to hydrochloric acid is 1:(0.5-6).

6. The full continuous-flow preparation method of claim 1, wherein in step (S2), flow rates of the second reaction mixture and the aqueous inorganic base solution are controlled such that a molar ratio of a cyclization product in the second reaction mixture to an inorganic base is 1:(1-10); a temperature of the micromixer is controlled to 0-40° C.; and the hydrolysis reaction is performed in the second continuous-flow reactor at 20-120° C. for 0.1-60 min.

7. The full continuous-flow preparation method of claim 1, wherein in step (S2), a temperature of the second continuous-flow reactor is controlled to −10-80° C., and a pressure of the second continuous-flow reactor is controlled to 0-1 MPa.

8. The full continuous-flow preparation method of claim 1, wherein in step (S2), a mass percentage of an inorganic base in the aqueous inorganic base solution is 5-50%; and the inorganic base is selected from the group consisting of lithium carbonate, sodium carbonate, potassium carbonate, lithium bicarbonate, sodium bicarbonate, potassium bicarbonate, ammonia, ammonium carbonate, ammonium bicarbonate, lithium bicarbonate, sodium bicarbonate, potassium bicarbonate, lithium hydroxide, sodium hydroxide, potassium hydroxide and a combination thereof.

9. The full continuous-flow preparation method of claim 1, wherein the first continuous filtration and reaction device and the second continuous filtration and reaction device are independently a continuous kettle filter, a continuous scraper filter, a continuous filter press and a continuous rotary disc filter or a combination thereof connected in series with a reactor.

10. The full continuous-flow preparation method of claim 1, wherein in step (S3), a molar ratio of the thiothiamine (5) to the hydrogen peroxide is 1:(0.9-5); and the oxidation reaction is performed in the third continuous-flow reactor at −10-50° C. and 0-1 MPa for 0.1-60 min.

11. The full continuous-flow preparation method of claim 1, wherein in step (S4), the filtration in the second continuous filtration and reaction device is performed at −15-30° C., and reaction between the second filter cake and the organic hydrochloric acid solution is performed at 20-100° C. and MPa 0-1 MPa for 0.1-60 min; and a molar ratio of the thiamine sulfate (6) in the second filter cake to hydrochloric acid 1:(0.9-5).

12. The full continuous-flow preparation method of claim 1, wherein in step (S4), the organic hydrochloric acid solution is selected from the group consisting of hydrochloride methanol solution, hydrochloride ethanol solution, hydrochloride ethylene glycol solution, hydrochloride propanol solution, hydrochloride acetone solution, hydrochloride ethyl acetate solution and hydrochloride dioxane solution.

13. The full continuous-flow preparation method of claim 1, wherein the first continuous-flow reactor, the second continuous-flow reactor and the third continuous-flow reactor are independently a microchannel continuous-flow reactor, a static tubular continuous-flow reactor, an oscillatory tubular continuous-flow reactor or an oscillatory plate-type continuous-flow reactor; an inner diameter of the static tubular continuous-flow reactor and the oscillatory tubular continuous-flow reactor is 1 mm-20 cm; and an inner diameter of the oscillatory plate-type continuous-flow reactor is 500 μm-5 cm.

14. The full continuous-flow preparation method of claim 1, wherein in step (S2), the micromixer is a static mixer, a T-type mixer, a Y-type mixer, a cross-type mixer, a coaxial flow mixer, a continuous stirring mixer or a flow-focusing mixer; the first continuous-flow reactor, the second continuous-flow reactor and the third continuous-flow reactor are each formed by one or more continuous-flow reactors connected in series or in parallel; and the first continuous filtration and reaction device and the second continuous filtration and reaction device are each formed by one or more continuous filtration and reaction devices connected in series or in parallel.

15. The full continuous-flow preparation method of claim 1, wherein the continuous-flow reaction system further comprises a first feed pump, a second feed pump, a third feed pump, a fourth feed pump, a fifth feed pump, a sixth feed pump, a seventh feed pump, a first control valve, a second control valve, a third control valve, a fourth control valve and a fifth control valve; an inlet of the first continuous-flow reactor is connected to the first feed pump, the second feed pump and the third feed pump; an outlet of the first continuous-flow reactor is connected to a first inlet of the first continuous filtration and reaction device; a second inlet of the first continuous filtration and reaction device is connected to the fourth feed pump through the first control valve; an outlet of the first continuous filtration and reaction device is connected to a first port of the second control valve; a second port of the second control valve is connected to a first filtrate collection pipeline; a third port of the second control valve is connected to the fifth feed pump; the fifth feed pump is connected to a first inlet of the micromixer; a second inlet of the micromixer is connected to the sixth feed pump; an outlet of the micromixer is connected to the second continuous-flow reactor; an outlet of the second continuous-flow reactor is connected to a first inlet of the second continuous filtration and reaction device through the third control valve; a second inlet of the second continuous filtration and reaction device is connected to the seventh feed pump through the fourth control valve; an outlet of the second continuous filtration and reaction device is connected to a first port of the fifth control valve; a second port of the fifth control valve is connected to a second filtrate collection pipeline, and a third port of the fifth control valve is connected to a target product collection pipeline.

* * * * *